United States Patent [19]

Herr et al.

[11] Patent Number: 5,605,803
[45] Date of Patent: Feb. 25, 1997

[54] HUMAN SPERM DIAGNOSTIC

[75] Inventors: John C. Herr, Charlottesville; Richard M. Wright, Palmyra, both of Va.

[73] Assignee: University of Virginia Alumni Patents Foundation, Charlottesville, Va.

[21] Appl. No.: 231,675

[22] Filed: Apr. 25, 1994

Related U.S. Application Data

[63] Continuation-in-part of Ser. No. 858,798, Mar. 27, 1992, which is a continuation-in-part of Ser. No. 481,491, Feb. 16, 1990, which is a continuation-in-part of Ser. No. 318,551, Mar. 3, 1989, abandoned.

[51] Int. Cl.$^6$ .................................................. G01N 33/567
[52] U.S. Cl. ........................... 435/7.21; 435/7.1; 435/7.9; 435/7.94; 436/518; 530/388.2
[58] Field of Search ............................... 435/7.21, 172.2, 435/240.27, 7.9, 7.94, 7.1, 7.3; 530/388.2; 436/518

[56] References Cited

U.S. PATENT DOCUMENTS

| | | |
|---|---|---|
| 4,741,998 | 5/1988 | Herr et al. |
| 4,782,136 | 11/1988 | Goldberg et al. .................. 530/326 |
| 5,047,508 | 9/1991 | Herr et al. ......................... 530/387 |

FOREIGN PATENT DOCUMENTS

| | | |
|---|---|---|
| 2012264 | 9/1990 | Canada. |
| 0204566 | 12/1986 | European Pat. Off. |

OTHER PUBLICATIONS

Kurth, B. E. et al. "Localization of Sperm Antigen SP–10 . . . " Biology of Reproduction 44:814–821, 1991.
Henry, J. B. Clinical Diagnosis and Management by Laboratory Methods. Philadelphia: WB Saunders, 1979, p. 2099.
Journal of Reproductive Immunology, vol. 10, pp. 231–257, 1987, Deborah J. Anderson, et al., "Monoclonal Antibodies To Human Trophoblast and Sperm Antigens: Report of Two WHO–Sponsored Workshops, Jun. 30, 1986—Toronto, Canada".
"Antibodies A Laboratory Manual," p. 61, 100–105, 116, and 580–581, 1988, Ed Harlow, et al.
Coaan et al (1986) J. Cell Biol. 103;1289–1297.
Hardy et al (1988) Biology of Reproduction 38:423–437.
Herr et al (1990) Biology of Reproduction 42:181–193.
Lei et al (1986) J. Reprod. Immunol. 9:261–274.
Liu et al (1989) Int. J. Andrology 12:451–463.
Adekunle et al (1989) Biol. Reprod. 40:127–134.
Doege et al (1987) JBC262(36):17757–17767.
Millan et al (1987) PNAS USA 84:5311–5315.
Young et al (1983) PNAS USA 80:1194–1196.
Yi et al (1991) Biol. Reprod. 44:332–337.
Nagae et al., *Fertility and Sterility*, 45:701–707. (1986).
Yudin et al., *Gamete Research*, 20:11–24 (1988).
Cross et al., *Gamete Research*, 15:213–226 (1986).
Abstract No. 225934, Anderson et al., *Journal of Reproductive Immunology*, 10:231–257 (1987).

*Biological Abstracts*, vol. 79(5) Abstract No. 44868, Kallajoki et al., International Journal of Andrology, 7:283–296 (1984).
Gould et al., *Developmental Biology*, 117:306–318 (1986).
*Biological Abstracts*, vol. 89, Abstract No. 120800, Herr et al., Biol. Reprod, 42:181–194 (1990).
*Biological Abstracts*, vol. 86(7), Abstract No. 75251, Yudin et al., Gamete Res., 20:11–24 (1988).
*Biological Abstracts,*. vol. 84(12), Abstract No. 124183, Mortimer et al., Reprod Fertil., 81:127–136 (1987).
*Biological Abstracts*, vol. 77(5), Abstract No. 39354, Working et al., J. Exp. Zool., 227:97–108 (1983).
Noland et al., *J. Biological Chemistry*, 264:13586–135900 (1989).
Sofer et al., *BioTechniques*, pp. 198–203 (Nov./Dec. 1983).
PCT Search Report dated Jul. 26, 1990.
Wright et al., *Biol. Reproduction*, 42:693–701 (1990).
Baba et al., *FEBS Letters*, 244:296–300 (1989).
Anderson et al., *Journal of Reproductive Immunology*, 10:231–257 (1987).
Herr et al., *J. Andrology*, 9:42 (1988). 13th Ann. Meet. Abst. #96.
Kallajoki et al., *International Journal of Andrology*, 7:283–296 (1984).
Kallajoki et al., *International Journal of Andrology*, 9:181–194 (1986).
Salonen et al., *International Journal of Andrology*, 10:731–739 (1987).
Kallajoki et al., *Biology of Reproduction*, 35:157–165 (1986).
Lee et al., *J. Reproductive Immunology*, 4:173–181 (1982).
Huneau et al., *International Journal of Andrology*, 11:13–24 (1987).
Primakoff et al., *Nature*, 335:543–546 (1988).
Herr et al., *Journal of Forensic Sciences*, 32:346–356 (1987).
Herr et al., *Biology of Reproduction*, 35:773–784 (1986).
Maruyama et al., *Journal of Andrology*, 6:127–135 (1985).
Wolff et al., *Fertility and Sterility*, 49:497–504 (1988).
Marx, *Science*, 240:1616–1618 (1988).
Moss, *ABA Journal*, pp. 66–70 (May 1988).

(List continued on next page.)

*Primary Examiner*—Christine M. Nucker
*Assistant Examiner*—Jeffrey Stucker
*Attorney, Agent, or Firm*—Oblon, Spivak, McClelland, Maier & Neustadt, P.C.

[57] ABSTRACT

A kit and method for detecting sperm production in a human male individual includes the provision of one or more antibodies for sperm tissue-specific protein antigen, such as SP–10, which can be combined with a sample suspected of containing sperm to permit the antibody and the antigen to bind. The binding event is determined directly or indirectly, which is indicative of the presence of sperm in the sample. The frequency of binding can also be determined by calibrating the means used to determine the binding event, so as to indicate sperm production at or above a given concentration. A variety of applications for the kit and method are described.

33 Claims, No Drawings

OTHER PUBLICATIONS

Gaensslen, "Indentification of Semen and Vaginal Secretions," *Sourcebook in Forensic Serology, Immunology, and Biochemistry,* 149–181 (1983).

Comhaire et al., "The Significance of Semen Analysis for the Evaluation of Male Fertility," in *Male Fertility: Diagnosis and Management,* pp. 34–47 (Date Unkown).

Wolf et al., *Biology of Reproduction,* 29:713–723 (1983).

Isojima et al., *Journal of Reproductive Immunology,* 10:67–78 (1987).

Yan et al., *American Journal of Reproductive Immunology,* 4:111–115 (1983).

Paul et al., *Clinical Reproduction and Fertility,* 1:235–240 (1982).

Hancock et al., *Journal of Reproductive Immunology,* 7:215–223 (1985).

Kyurkchiev et al., *Immunology,* 57:489–492 (1986).

Isojima et al., *Clin. Exp. Immunol.,* 49:449–456 (1982).

Isojima et al., *Immunological Approaches to Contraception and Promotion of Fertility,* (Talwar Ed.), 323–333 (Plenum Publishing, 1986).

Chang et al., *Science,* 240:324–326 (1988).

Anderson et al., *Fertility and Sterility,* 40:557–571 (1983).

Naz, *Journal of Reproductive Immunology,* 11:117–133 (1987).

Yanagimachi, "Mammalian Fertilization," in *The Physiology of Reproduction,* (Knobil et al. Eds.), pp. 135–185 (Raven Press 1988).

HUMAN SPERM DIAGNOSTIC

This application is a continuation-in-part of U.S. patent application Ser. No. 07/858,798, filed Mar. 27, 1992, which is a continuation-in-part of U.S. patent application Ser. No. 07/481,491, filed Feb. 16, 1990, which is a continuation-in-part of U.S. patent application Ser. No. 07/318,551, filed Mar. 3, 1989, now abandoned.

BACKGROUND OF THE INVENTION

This invention pertains to a diagnostic for the presence and/or level of human sperm in a biological sample. Specifically, monoclonal or polyclonal antibodies for a sperm tissue-specific antigen associated with the head of human sperm are employed to determine the presence, absence and/or level of human sperm in an ejaculate or other sperm-containing biological sample. Methods, as well as diagnostic kits for medically unsupervised home testing are provided.

FIELD OF THE INVENTION

SP-10 is a sperm-specific antigen identified as an acrosomal constituent present throughout spermiogenesis. The SP-10 gene has been localized to human chromosome 11, and to the junction of bands q23–24. Substantial investigation by the inventors herein has established the tissue-specific nature of this antigen. The highly specific character of this antigen is reviewed in publications after development of the invention, e.g., *Freemerman et al, Biology of Reproduction* 50, 615–621 (1994) and is addressed as well in other publications by the inventors herein, see, e.g., Kurth et al, *The Anatomical Record*, 236, 619–625 (1993). The amino acid sequence for this antigen is set forth, Wright et al, *Biology of Reproduction*, 42:693–201 (1990) and U.S. patent application Ser. No. 07/481,491, by the inventors herein, currently pending. The entire disclosure of this application is incorporated herein by reference.

A monoclonal antibody specific for this tissue-specific antigen has been previously developed, identified as MHS-10. This monoclonal antibody is expressed by a hybridoma cell line deposited at the American Type Culture Collection, 12301 Parklawn Drive, Rockville, Md., under accession number ATCC HB 10039. This monoclonal antibody is discussed extensively in the aforereferenced U.S. patent application Ser. No. 07/481,491.

Previous scientific research and commercial developments in the investigation of fertility, pregnancy, problems and syndromes associated therewith, have focused on the female reproductive cycle. Until recently, determinations of pregnancy or ovulation had to be done through an office visit to a licensed medical practitioner. The cost, and lack of privacy associated with such visits have lead directly to the incredible success of "home test kits" which are in fact kits requiring simple and straightforward manipulation of a test sensitive to the presence of human chorionic gonadotropin (HCG) for pregnancy or luteinizing hormone (LH) for ovulation.

At the same time, issues of family planning, and methods of addressing a couple's lack of fertility, have focused increasing attention on male fertility, problems associated therewith, and medical procedure addressing the same. Currently, one element commonly addressed when a couple experiences difficulty in achieving conception is an investigation into the male partner's sperm viability and count. This requires a high-cost trip again to a licensed facility, coupled with the need to collect an ejaculate sample for microscopic examination (more frequently, a series of samples) under conditions that are frequently considered, in the current culture, humiliating or at least embarrassing. In this regard, the loss of privacy associated with such testing is of particular importance.

As a method of contraception, optional vasectomies, because of their generally "out-patient character", reliability, and relatively low risk have become increasingly popular. The principal method of monitoring and verifying the effectiveness of a vasectomy, and the absence of sperm from the reproductive tract, are repeated microscopic examination of semen samples in an andrology laboratory, again associated with a relative high cost and loss of privacy. Yet, confirmation of sperm-free ejaculation for a period of time is required, before other methods of contraception can be discontinued.

Advances in medical technology have improved the reliability of vasovastosomy, a surgical vasectomy reversal, in which the previously severed ends of the vas deferens are reconnected. Again, the question of whether the surgery has been successful requires microscopic monitoring, over an extended period of time, to ensure a return to normal sperm levels, and fertility, after the operation. Again, this imposes an increase in costs, and a frequently embarrassing or humiliating loss of privacy.

The success of the home urine test kits for pregnancy and ovulation, coupled with the persistent and increasing importance of determining male fertility, and the presence or absence of sperm, coupled with the high cost of current methods of determining the same, clearly points up the need for a home test kit for men, similar to those available for female reproduction that would allow the easy, rapid and low-cost determination of the presence of sperm in a biological sample. To date, this need has not been met.

SUMMARY OF THE INVENTION

The above objectives, and additional objectives made clear by the discussion set forth below, are met by provision of an assay which permits the quick and easy determination of the presence of human sperm in an ejaculate or other biological sample, by testing for the presence/absence, and/or amount of the reaction between the SP-10 antigen and monoclonal antibody(ies) specific therefore, which reaction is determined in a readily noticeable fashion. This permits the assay or testing to be conducted in privacy, without the intervention of trained medical practitioners, and at relatively low cost. It provides a preliminary indication that permits the individual to take further action, or to seek expert medical advice, depending on the results obtained. The ejaculate, or a biological sample containing the remnants of an ejaculate, such as a sample from post-intercourse vaginal lavage is added to a preparation including one or more monoclonal antibodies specific for the SP-10 antigen or other sperm specific antigen. The antibodies may be polyclonal or monoclonal. Presence of sperm in the sample tested gives rise to binding between the antibody and the SP-10 antigen of the sperm, a binding reaction which is detected, directly or indirectly, through a variety of methodologies. The most familiar type of assay includes a colorimetric assay, wherein the antibody is labelled with a reporter molecule which can be detected by a specific color. The binding reaction either induces a color or color change, or the color is developed with a second agent, generally an enzyme. As the reporter molecule is "developed", that is, the appropriate color is induced, only in the presence of bound antibody, a positive reaction is indicative of the presence of sperm, as the antigen has been demonstrated to be tissue specific. Absence of the desired color, or a different color, is indicative of a "negative" result, that is, an absence of the antigen, and therefore sperm, from the sample.

Among the easiest assays of this type to perform are the solid-phase immunoassays, in which the primary antibody is bound to a surface, such as a membrane or bed, which is then exposed to the sample suspected of having, or lacking, sperm. Sperm present in the sample will be bound by the monoclonal antibody, termed the primary antibody. Unbound material is washed or removed from the sample, followed by addition of a secondary antibody which also binds to the sperm, and which bears a label, an enzyme or enzyme substrate. The secondary antibody need not bind to the same epitope as the primary antibody. After allowing binding to occur, the sample is again washed, and the counterpart of the enzyme or substrate is added (When the secondary antibody is bound to an enzyme, the substrate is added. When the substrate is bound to the secondary antibody, the enzyme is added.). The enzyme cleaves a portion of the substrate, causing the substrate to undergo a color change, to chemiluminesce, to fluoresce, or other readily detectable phenomenon. The various elements of the assay, that is, the bound primary antibody, the labelled secondary antibody, and the substrate, can be provided in a single kit, to provide for home use. Both direct, and indirect evidence of the presence of the sperm can be relied on to indicate potential fertility, or an absence thereof.

The testis and sperm specific marker protein provided by this invention lends itself to a wide variety of applications. Thus, males concerned about the possible persistence of sperm after a vasectomy, or the reappearance of the sperm in the ejaculate subsequent to a vasovastosomy can conveniently investigate for the presence of sperm at home. Similarly, a female having intercourse can investigate the presence of sperm in the ejaculate of her partner, by testing for the presence or absence of sperm in a vaginal lavage following intercourse. This, for example, allows independent verification, by the woman, of her partner's statement that he has been vasectomized, or the opportunity to determine whether the partner may be infertile in the event a subsequent pregnancy is desired.

Three monoclonal antibodies for use as primary antibodies for assays of this type have been developed and deposited pursuant to Budapest Treaty conditions. In addition to MHS-10, two additional monoclonal antibodies, 3C12 and 6C12 have been developed, and are expressed by hybridoma cell lines 3C12-DLC6 and C12-A1A8, deposited under Budapest Treaty conditions, at the American Type Culture Collection under ATCC designations HB 11541 and HB 11542, respectively. Additional monoclonal antibodies may be raised in the same fashion, as disclosed in U.S. patent application Ser. No. 07/481,491. Polyclonal antibodies may be raised in similar fashion.

DETAILED DESCRIPTION OF THE INVENTION

The essential aspect of the diagnostic and assay of this invention is the binding reaction between an antigen that is sperm-specific, that is, found on or in connection with spermatids and sperm, and sperm only, and a antibody (monoclonal) specific thereto. In U.S. patent application Ser. No. 07/481,491, methods are disclosed for raising antibodies to "antigens" of this type, that is, protein specific for sperm. Generally, a host animal, such rabbits, rats, mice, etc, are immunized with a sperm preparation containing the desired antigen, and then antibody-producing cells, such as B lymphocytes from the host's spleen are fused with tumor cells, to produce hybridomas. Exemplary tumor cells include rat myeloma and mouse plasmacytoma cells. The hybridomas are then screened for antibody-expression, using the antigen preparation used to immunized the host. MHS-10, 3C12 and 6C12 have been raised in this fashion.

Other monoclonal or polyclonal antibodies may be raised to SP-10 by purifying the native SP-10 antigen from human sperm using monoclonal antibody affinity chromatography with bound MabMHS-10, 3C12, or 6C12 followed by further purification by reverse phase HPLC, using the protocol of Herr et al, 1992 *Biol. of Reprod.* 47:11–20. The native SP-10 is then injected into a host until serum antibody is detected to the antigen. Additional monoclonal antibodies may be generated by fusing the host's spleen cells to tumor cells to produce hybridomas.

Alternatively other monoclonal or polyclonal antibodies may be developed to a recombinant SP-10 antigen produced in an appropriate eukaryotic or prokaryotic expression vector such as discussed in copending U.S. patent application Ser. No. 08/292,045. To date the SP-10 protein has been expressed in the lab in PWR 590, pGEX as well as pMAL and pET [Reddi et al, 1994]. Rabbit and monkey polyclonal antibodies have been made to recombinant SP-10 produced in PWR590. Baboon polyclonal antibodies have been made to recombinant SP-10 produced in pMal, pGEX and pET. The mouse monoclonal antibodies 3C12 and 6C12 which we recently deposited were made to recombinant SP-10 produced in pGEX. Thus, additional monoclonal or polyclonal antibodies may be made by immunizing animals with full or partial length recombinant SP-10. Depending on the length of the SP-10 recombinant insert expressed in these vectors and subsequently inoculated, antibodies may be generated to various determinants on either the full or partial length SP-10 polypeptides.

Once specific monoclonal antibodies have been developed, the preparation of mutants and variants thereof, by conventional techniques, is also available. It should be noted that the three deposited antibodies referred to herein appear to exhibit binding to different epitopes of the SP-10 antigen, and thus, myriad other monoclonal antibodies can similarly be raised.

Similarly, as disclosed in U.S. patent application Ser. No. 07/481,491, the entire SP-10 antigen need not be present to achieve binding. Fragments of the SP-10, if present, will be bound by the antibody. A wide variety of immunogenic fragments are disclosed in the referenced application. Other sperm-specific antigens, rather than SP-10, can also be employed, in the use of this invention. Exemplary antigens include human S71 protein, human PH30 protein and mitochondrial capsule seleno-protein (rat). Polyclonal and monoclonal antibodies are raised against these proteins (or epitopic determinant fragments thereof) in similar fashion. The fundamental requirements for this invention is at least one antibody specific for a sperm-specific protein or protein fragment. MHS-10, 3C12 and 6C12, as monoclonal antibodies, and SP-10, as the antigen, are but one example of potential combinations.

In the invention, the monoclonal antibody is contacted with the sample, under conditions (aqueous sample, ambient temperature and normal atmosphere) which permit the antibody-antigen binding reaction to occur. After sufficient reaction time has passed, a secondary antibody is added to the preparation, which will also bind to the antigen in question. The secondary antibody bears a label or reporter molecule, such as an enzyme or enzyme substrate, and is similarly allowed to bind to the antigen bound by the primary antibody. Unbound material is removed, generally by pouring off the sample (the primary antibody can be bound to a solid surface, to make the assay simpler and more "user friendly"). Desirably, the enzyme is bound to the secondary antibody.

Unbound secondary antibody is poured or washed off, and a substrate which changes color, chemiluminesces, fluoresces, or undergoes some other readily detectable change in the presence of the enzyme, due to the action of the enzyme on the substrate, is then added. Save for the use of SP-10 and the monoclonal antibodies MHS-10, 3C12 and 6C12, formats of this type, and assays employing the same are well known and do not constitute an aspect of this invention, per se. Representative enzyme immunosorbent assays (EIA) are set forth in U.S. Pat. No. 5,149,622, which employs an improved surface on which to conduct the assay, and is incorporated herein by reference. Other solid and liquid phase assay methodologies may be employed without the exercise of inventive skill.

One embodiment of the home kit follows the capture assay format where the monoclonal antibody MHS-10 is bound to a solid phase and used to capture the SP-10 antigen. Recognition of the SP-10 antigen may be completed by use of a second monoclonal or polyclonal immunoreagent, Shen et al, 1993, *Am. J. Reprod. Immunology*, 29:231–240 (1993), coupled to a reporter enzyme or a third immunoreagent is employed in a sandwich.

Another envisioned assay format would utilize a wick [dip stick] and antibody coated colored beads. A drop of ejaculate [with released SP-10] will be applied to a sample of colored beads containing antibody and the beads with SP-10 bound will migrate through a wick until they are captured by a second antibody to SP-10.

Another envisioned assay format would utilize antibody coated colored magnetic beads. In this assay, the magnetic beads are coated with the monoclonal or polyclonal antibody to SP-10. The beads, mixed with semen and SP-10, are captured by the antibody. A magnetic dipstick may be used to recover the magnetic beads. The colored magnetic beads are then freed of the magnet and allowed to migrate in the wick to a zone of secondary antibody which captures the beads resulting in a colored line.

In another assay format, an assay wick is coated with two monoclonal antibodies; one to the sperm surface, the other monoclonal would be to SP-10. The antibodies may be sprayed onto the wick very close to one another. One monoclonal antibody captures the sperm. The sperm are then treated to lyse the acrosome. The second antibody captures SP-10 released after SP-10 lysis. The wick is then be briefly washed. A second anti-SP-10 mono or polyclonal antibody with enzyme conjugate may be used to develop a colored reaction product.

In another assay format, a specialized glass bead with microspikes is used. The microspikes, silanized, are coupled with an anti-SP-10 antibody. The beads are mixed with sperm to both puncture the acrosome and capture the SP-10 antigen. The glass beads will again be wicked up and detected as a line or spot with a secondary antibody to SP-10.

The now-established tissue specificity of SP-10, as well as the antigen specificity of the monoclonal antibodies employed herein, lends itself to a variety of assays wherein sensitivity and reliability are of paramount importance. Each of these applications, both the preparations therefor and the assay methods provided, constitute an aspect of this invention.

FORENSIC APPLICATIONS

The law and procedures concerning sexual assault and evidence relevant thereto, has undergone a dramatic change in the last few years. One essential element of evidence in bringing a rape or sexual assault charge is establishing the presence of sperm in or on the alleged victim. A traditional "christmas tree stain" method has been used in connection with assays to determine the presence of sperm, but is difficult to use in a variety of situations where the sperm are present in relatively few numbers (e.g., anal swabs in cases of pedophilia). Thus, preliminary evidence of a sexual assault can be provided relatively directly, with a high degree of reliability, even in particularly small samples. Because this application calls for development of the evidence under controlled forensic conditions, indirect detection methods, such as staining procedures and the like can be substituted for the direct colorimetic, chemiluminescent, fluorescent, etc. assays discussed above.

GERM CELL LINEAGE MONITORING

As noted, the SP-10 "antigen" or protein arises in round spermatids in the testes, and persists through all steps of sperm differentiation. Thus, monoclonal antibodies for this protein can be used to identify not only mature sperm, but cells of spermatogenic lineage, either in the ejaculate, or in tissue biopsies. Investigations into male infertility increasingly suggest a correlation between male infertility and abnormal numbers of immature cells of one or more stages in the spermatogenic lineage. The "antigen" antibody binding reaction of this invention provides a method to monitor not only sperm cells, but immature spermatogenic cells, to provide additional information on current, or incipient infertility due to abnormal numbers of immature spermatids being produced.

Home Test Kit

There are a variety of situations in which a test that could be done at home, or in privacy, without the intervention of a medical or scientific practitioner, would be desirable. That in fact such applications are particularly desirable can be confirmed by reference to the enormous success of the home colorimetric urine test for pregnancy, in which the presence or absence of HCG is indicated through a colorimetric test that is quickly and conveniently done by the female wishing to determine whether she is pregnant or not. Similarly, as discussed in detail below, there are a variety of situations where it would be desirable to be able to determine whether an individual's ejaculate in fact contains sperm, and if so, whether the sperm approaches a threshold value necessary for practical fertility. In these assays, as with the assays discussed above, the presence or absence of sperm can be determined by using one or more monoclonal antibodies specific for a sperm tissue-specific antigen or protein, such as SP-10. Where it is necessary to evaluate whether or not sperm are present in a particular concentration or level, it is fairly easy to calibrate such a test to a standard, below which the reaction is not clearly detectable or visible. In the alternative, where the threshold value is positive, the signal can be reinforced or caused again to change color. The essence of this testing is again the contacting of a sample suspected of containing human sperm with a monoclonal antibody specific for a sperm-specific protein. A non-limiting description of various needs met by this invention is discussed below.

Infertile Adult Couples

Frequently, a couple experiencing difficulty in achieving conception, prior to engaging the services of a professional, such as an infertility specialist, would prefer to determine if the difficulty in conceiving a child is due at least in part to infertility, or reduced fertility, in the male partner. In such a situation, a two-test kit can be provided, wherein the "first" test is calibrated to give a positive reaction or signal if the concentration of sperm is at appropriate "normal" levels of about $10^8$ or above. Sensitivity can be controlled in a variety of fashions, including controlling the nature of the reporter molecule. The less sensitive the reporter molecule is, the greater concentration of antigen, and thus, binding ligand pairs is necessary to trigger a "positive" value. If this test is positive, the conclusion that the male partner has a normal sperm count can be arrived at. Thus, a positive result might suggest attention of a medical practitioner be directed to the female partner first.

If the test of the "low sensitivity" assay is negative, a second test calibrated to detect sperm in a much lower concentration, i.e., $10^5$–$10^6$ could be conducted. If this test were positive indicating a low sperm count or following an entirely negative result indicating the absence of sperm in the low-sensitivity assay, specific counseling would be suggested in the materials provided with the kit.

Vasectomized Males

Males having undergone a vasectomy are required to clear their reproductive tracts of sperm for an extended period of time, prior to discarding or discontinuing other methods of contraception. A test kit for determining the presence of sperm by reaction with a monoclonal antibody to the sperm-specific protein would eliminate the need for high-cost testing of the ejaculate over this period of time. In this embodiment, testing over the recommended time period could be conducted using one product kit provided with a series of assays, or a series of identical assay kits could be provided, to allow the male to monitor the progress of sperm clearance from the reproductive tract. If the test continues to be positive beyond a reasonable period for clearance, a physicians visit would be recommended.

Because spontaneous recanalization of the cut ends of the vas is possible following a vasectomy, an event which may result in a return to fertility, periodic monitoring of the vasectomized patient for the appearance of sperm using home assay kits, would alert the patient that a recanalization had occurred and the possibility of conception had returned. Because recanalization is a possible cause of patient dissatisfaction with the vasectomy procedure and a just cause of physician liability, such a home kit would be of benefit from both the patient and physician viewpoints.

Vasovasostomized Males

A male having undergone a vasectomy may undergo a surgical procedure, vasovastosomy, in which the severed ends of the vas deferens are surgically reconnected. In some cases, the success of the procedure is problematic, and in all cases, a return to normal levels of sperm in the ejaculate must be monitored to conclude that the operation is completely successful. A kit designed to perform this test would be calibrated to normal sperm levels, such that a positive indication would be confirmation of the success of the operation, avoiding the need for relatively expensive and inconvenient physician monitoring.

Validation of sperm levels by females

For many females, the question of whether or not her male sexual partner is fertile, particularly where the possibility of a vasectomy is involved, is one that she cannot currently independently determine. The assay disclosed herein provides an opportunity for a female sexual partner to confirm her male partner's claim of a prior vasectomy, or in the alternative, determine the existence of sperm in a potential partner, where fertility is a consideration.

Thus, following intercourse, a sample taken from a vaginal lavage or douche can be obtained in privacy. The sample is introduced to the monoclonal and/or polyclonal antibody test kit, in the same way that the ejaculate is introduced. Calibrated to the reduced concentration that will naturally occur in such a sample, the test kit allows the female to immediately determine the reliability of her partner's vasectomy claim, or, in the alternative, the fertility capability of her male partner. Because of the rapid nature of the test, and the ability to conduct it immediately after intercourse, appropriate measures can be taken where necessary.

Determination of Sperm Production

For a variety of reasons, independent of a vasectomy or other outside influences, a male may wish to determine whether or not sperm are being produced. Thus, a male individual undergoing puberty, or an older male, such as a college student, embarking on a romantic encounter and desiring to know if he is manufacturing sperm, could use the assay, calibrated to give a positive response in the presence of normal levels of sperm tissue-specific antigen. At the other end of the life cycle, an elderly male who has remarried or otherwise desires to determine whether or not he has the potential to father children, or otherwise, for independent reasons, again, by calibrating the sensitivity of the assay to normal, below normal, or above normal levels, a variety of information can be quickly lucidated without substantial expense.

Impact of Trauma or Chemical Agents

In a variety of situations, trauma to the testis, and/or the use of chemical agents, may compromise sperm production. Thus, after testicular trauma, after mumps orchitis and related situations, including testicular and spermatic cord torsion, an assay calculated to below normal levels, or normal levels, could be used to detect possible loss of function. Additionally, progressive recovery, or progressive damage could also be monitored.

A similar situation is presented by athletes undergoing intense training, and/or athletes using anabolic steroids. Both situations present the possibility of reduced sperm production, or loss of sperm production. To monitor whether or not training and/or anabolic steroid use has reduced sperm levels, the individual would conduct a first assay or test prior to undertaking the athletic regime, and then periodically throughout the regime, conduct an identical test calibrated for the same level. A negative response developed during the course of the program, after a positive response, prior to beginning the program, would be indicative of endangerment of sperm production.

Environments, particularly work environments, frequently pose potential threats to sperm production that are difficult to monitor with available assays, and are simultaneously difficult to talk about and consider. Thus, workers routinely exposed to high risk environments, such as those involved with radiation, pilots and others exposed to hyperbaric oxygen, anesthesiologists and anesthetists, workers exposed to toxins, and the like could be provided with a kit on a periodic basis, e.g., every few months, to test themselves at home for continuing sperm production. This low-cost alternative, which provides privacy and confidentiality to the individual, might be used to establish new levels of care in these industries. Similarly, military personnel exposed, either through testing or in the field, to radiation or toxins could rapidly, inexpensively check for effects on sperm production.

Infections, Obstructions and Surgery on the Reproductive Tract

The male reproductive tract is subject to a variety of infections and surgical conditions, which threaten sperm production. Thus, viral or bacterial infections such as gonorrhea or chlamydia infections may raise concerns as to continuing levels of sperm production. During and following treatment of the infection, a quick and easy assay using monoclonal and/or polyclonal antibodies for sperm specific antigens would allow reassurance that normal function continues.

Similarly, the male reproductive tract is subject to a variety of obstructions, which may be due to infection, a tumor, congenital obstructions and other sources. A quick sperm specific antigen assay for use in the surgical suite could be used to determine whether the site selected by the physician for treatment and correction of the obstruction is above or below the obstruction. The fluid aspirated from the site would be assayed for the presence of SP-10 or other sperm tissue-specific antigen calibrated to very high sensitivity values. A positive response would clearly indicate that the site lies between the obstruction and the testes.

In addition to the use during the surgery itself, following the correction of the obstruction, the assay of the invention can be used to confirm normal sperm production, by using an assay calibrated to normative sperm levels.

Monitoring Male Contraceptives

A variety of systemic male contraceptives, and contraceptive vaccines are currently under study. The vaccine candidates include FSH, inoculation with which generates the production of FSH antibodies resulting in reduced FSH levels, which in turn results in markedly reduced sperm counts in the ejaculate. Another vaccine agent, GnRH (gonadotropin releasing hormone) currently under development results in a reduction of testosterone through endocrine control and again sperm production is dramatically lowered. To monitor the effectiveness of these vaccines, sperm numbers can be easily determined through the assay of this invention.

Testosterone implants are also currently being tested as male contraceptives, again resulting in a decrease in FSH as well as LH, which in turn reduces spermatogenesis. The assay of this invention can be used to monitor both the effectiveness of the implant, and the return to normal sperm levels, upon exhaustion or withdrawal of the implant.

The examples set forth above are not limiting, and a variety of materials, methods and other applications are readily imagined. Assays requiring more complicated manipulations, sophisticated machinery and education are also possible, such as radio immunoassays, spectrophotometric assays involving emission spectra shifting surface plasma resonance, biosensous, and the like. These assays offer enhanced reliability and the ability to discriminate between various levels of response. All such assays, and the kits for conducting those assays, are characterized by the same essential elements, that is, a sperm tissue-specific antigen or protein, a primary monoclonal antibody selective therefore, and a means for detecting binding therebetween, which can be sensed to give a readily detectable indication of its presence. Beyond this, the invention is not limited, save for recitations appearing in the claims below.

What is claimed is:

1. A method for determining the concentration of sperm present in the ejaculate of a male human individual, comprising:

combining an ejaculate sample from said individual with a preparation comprising a first antibody specific for a testes-specific and sperm tissue-specific protein antigen, under conditions which permit said antibody to bind any said antigen present in said sample, and inspecting said combined sample to determine the frequency of said binding, wherein the frequency of occurrence of said binding is indicative of the total sperm concentration in said ejaculate.

2. The method of claim 1, wherein said antibody comprises a monoclonal antibody.

3. The method of claim 1, wherein said antibody comprises a polyclonal antibody.

4. The method of claim 1, wherein said step of determining the frequency of said binding is made by detecting a readily detectible signal.

5. The method of claim 4, wherein said signal is colorimetric, flurometric, or chemiluminescent.

6. The method of claim 1, wherein said antigen is SP-10.

7. The method of claim 6, wherein said antibody is the antibody expressed by the hybridoma cell line of a deposit selected from the group consisting of ATCC HB 10039, ATCC HB 11541, and ATCC HB 11542.

8. The method of claim 1, wherein said method further comprises removing substantially all said sample not bound to said antibody, adding to said first antibody and any material bound thereto a second antibody which binds to said antigen and is complexed with a reporter substance, allowing said second antibody to bind to said antigen, removing all unbound second antibody, and detecting the presence of said reporter substance.

9. The method of claim 8, wherein said reporter substance is an (A) enzyme or a (B) enzyme substrate, and wherein the presence of said reporter molecule is determined by addition of either of B or A, whichever said reporter molecule is not, and detecting a reaction between A and B.

10. The method of claim 9, wherein the reaction of A and B gives rise to the formation of a color, a change in color, fluorescence, a change in fluorescence, or emission of visible light.

11. A method of determining whether or not sperm are present in a biological sample, comprising combining said sample with a preparation comprising a first antibody which is specific for a testes and sperm tissue-specific protein antigen, which is present throughout spermiogenesis under conditions which permit said antibody to bind to any said antigen present in said sample, and inspecting said combined sample to determine the existence of any said binding, wherein the presence of said binding is confirmation of the presence of sperm in said sample.

12. The method of claim 11, wherein said antibody comprises a monoclonal antibody.

13. The method of claim 11, wherein said antibody comprises a polyclonal antibody.

14. The method of claim 11, wherein said sample is obtained from a living organism.

15. The method of claim 14, wherein said sample is obtained from a human female.

16. A kit for detecting the presence of sperm in a biological sample, comprising:

(1) a surface on which said sample may be deposited, (2) an antibody specific for a testes and sperm tissue-specific protein antigen present throughout spermiogenesis, and (3) a means for indicating binding of said monoclonal antibody to antigen present in said sample.

17. The kit of claim 16, wherein said antibody is bound to said surface.

18. The kit of claim 16, wherein said means for indicating comprises a second antibody which will bind to said sperm tissue-specific antibody antibody when bound to said antibody, which second antibody is complexed with a reporter substance.

19. The kit of claim 16, wherein said antibody comprises a monoclonal antibody.

20. The kit of claim 16, wherein said antibody comprises a polyclonal antibody.

21. The kit of claim 18, wherein said reporter substance is an enzyme or an enzyme substrate.

22. The kit of claim 21, wherein said kit further comprises a second substance which reacts with said reporter substance to generate a visibly detectable signal.

23. The kit of claim 16, wherein said antibody is selected from the group consisting of monoclonal antibodies expressed by the hybridoma cell line deposited under accession number ATCC HB 10039, ATCC HB 11541, and ATCC HB 11542.

24. A method of determining the presence of sperm above a predetermined concentration, in the ejaculate of a male human individual, comprising:

combining an ejaculate sample from said individual with a preparation comprising a first antibody specific for a protein antigen which is testes and sperm tissue-specific under conditions which permit said antibody to bind to any said antigen present in said sample, and inspecting said combined sample to determine if the frequency of said binding exceeds a value corresponding to said predetermined threshold.

25. The method of claim 24, wherein said antibody comprises a monoclonal antibody.

26. The method of claim 24, wherein said antibody comprises a polyclonal antibody.

27. The method of claim 24, wherein said step for determining the frequency of said binding is made by detecting a readily detectible signal.

28. The method of claim 27, wherein said signal is colorimetric, fluorometric or chemiluminescent.

29. The method of claim 24, wherein said antigen is SP-10.

30. The method of claim 24, wherein said antibody is the antibody expressed by the hybridoma cell line of a deposit selected from the group consisting of ATCC HB 10039, ATCC HB 11541 and ATCC HB 11542.

31. The method of claim 24, wherein said method further comprises removing substantially all said sample not bound to said antibody, adding to said first antibody and any material bound thereto a second antibody which binds to said antigen and is complexed with a reporter substance, allowing said second antibody to bind to said antigen, removing all unbound second antibody, and detecting the presence of said reporter substance.

32. The method of claim 31, wherein said reporter substance is an (A) enzyme or (B) enzyme substrate, and wherein the presence of said reporter molecule is determined by addition of either of (A) or (B), whichever said reporter molecule is not, and detecting a reaction between (A) and (B).

33. The method of claim 32, wherein the reaction of (A) and (B) gives rise to the formation of a color, a change in color, fluorescence, a change in fluorescence, or emission of visible light.

* * * * *